United States Patent
Banks et al.

(10) Patent No.: US 8,480,856 B2
(45) Date of Patent: Jul. 9, 2013

(54) FLUOROMETRIC METHOD FOR MONITORING SURFACE ADDITIVES IN A PAPERMAKING PROCESS

(75) Inventors: Rodney H. Banks, Aurora, IL (US); Zhiyi Zhang, Naperville, IL (US); James L. Thomas, Heber Springs, AR (US)

(73) Assignee: Nalco Company, Naperville, IL (US)

( * ) Notice: Subject to any disclaimer, the term of this patent is extended or adjusted under 35 U.S.C. 154(b) by 108 days.

(21) Appl. No.: 13/243,130

(22) Filed: Sep. 23, 2011

(65) Prior Publication Data

US 2012/0031577 A1    Feb. 9, 2012

Related U.S. Application Data

(63) Continuation-in-part of application No. 12/047,736, filed on Mar. 13, 2008, now abandoned, which is a continuation-in-part of application No. 11/942,065, filed on Nov. 19, 2007, now abandoned.

(51) Int. Cl.
   *D21F 7/06*     (2006.01)
   *D21F 11/00*    (2006.01)
   *G01N 21/64*    (2006.01)

(52) U.S. Cl.
   USPC ........ 162/263; 162/158; 162/198; 422/82.08; 250/461.1; 356/317

(58) Field of Classification Search
   USPC ................. 162/158, 198, 252, 253, 259, 263, 162/380; 422/82.07, 82.08; 250/458.1, 459.1, 250/461.1; 336/317, 318
   See application file for complete search history.

(56) References Cited

U.S. PATENT DOCUMENTS

| | | | | |
|---|---|---|---|---|
| 3,956,630 A | * | 5/1976 | Mellows | 250/302 |
| 4,501,642 A | * | 2/1985 | Wells | 162/198 |
| 4,783,314 A | * | 11/1988 | Hoots et al. | 422/3 |
| 4,814,198 A | * | 3/1989 | Baecklund | 427/9 |
| 5,073,714 A | * | 12/1991 | Nguyen | 250/341.7 |
| 5,087,670 A | * | 2/1992 | Melancon et al. | 525/326.2 |
| 5,162,131 A | * | 11/1992 | Rantanen et al. | 427/10 |
| 5,413,719 A | * | 5/1995 | Sivakumar et al. | 210/708 |
| 6,682,810 B1 | * | 1/2004 | Jones et al. | 428/323 |
| 7,154,603 B2 | * | 12/2006 | Banks | 356/417 |

(Continued)

FOREIGN PATENT DOCUMENTS

| | | | | |
|---|---|---|---|---|
| GB | 1348638 A | * | 3/1974 | |
| JP | 2011118457 A | * | 6/2011 | |
| WO | WO 9951817 A1 | * | 10/1999 | |
| WO | WO 0186064 A1 | * | 11/2001 | |
| WO | WO 2008054297 | * | 5/2008 | |

OTHER PUBLICATIONS

Machine translation of JP 2011-118457, Advanced Industrial Property Network, Japan Patent Office, [online], [retrieved on Feb. 8, 2013]. Retrieved from the Internet: <URL: http://dossier1.ipdl.inpit.go.jp/AIPN/odse_top_dn.ipdl?N0000=7400 >.*

*Primary Examiner* — Mark Halpern
*Assistant Examiner* — Dennis Cordray
(74) *Attorney, Agent, or Firm* — Calfee, Halter & Griswold LLP

(57) ABSTRACT

An apparatus for and method of monitoring and optionally controlling the addition of one or more surface additives to a papermaking process via fluorometric means is disclosed.

15 Claims, 12 Drawing Sheets

U.S. PATENT DOCUMENTS

2002/0039181 A1* 4/2002 Shakespeare et al. ....... 356/73.1
2006/0160226 A1* 7/2006 Johnson .......................... 436/56
2006/0160227 A1* 7/2006 Sethumadhavan et al. ..... 436/56
2010/0132900 A1* 6/2010 Andersson et al. ............. 162/49

* cited by examiner

Optical Assembly of Sheet Fluorometer

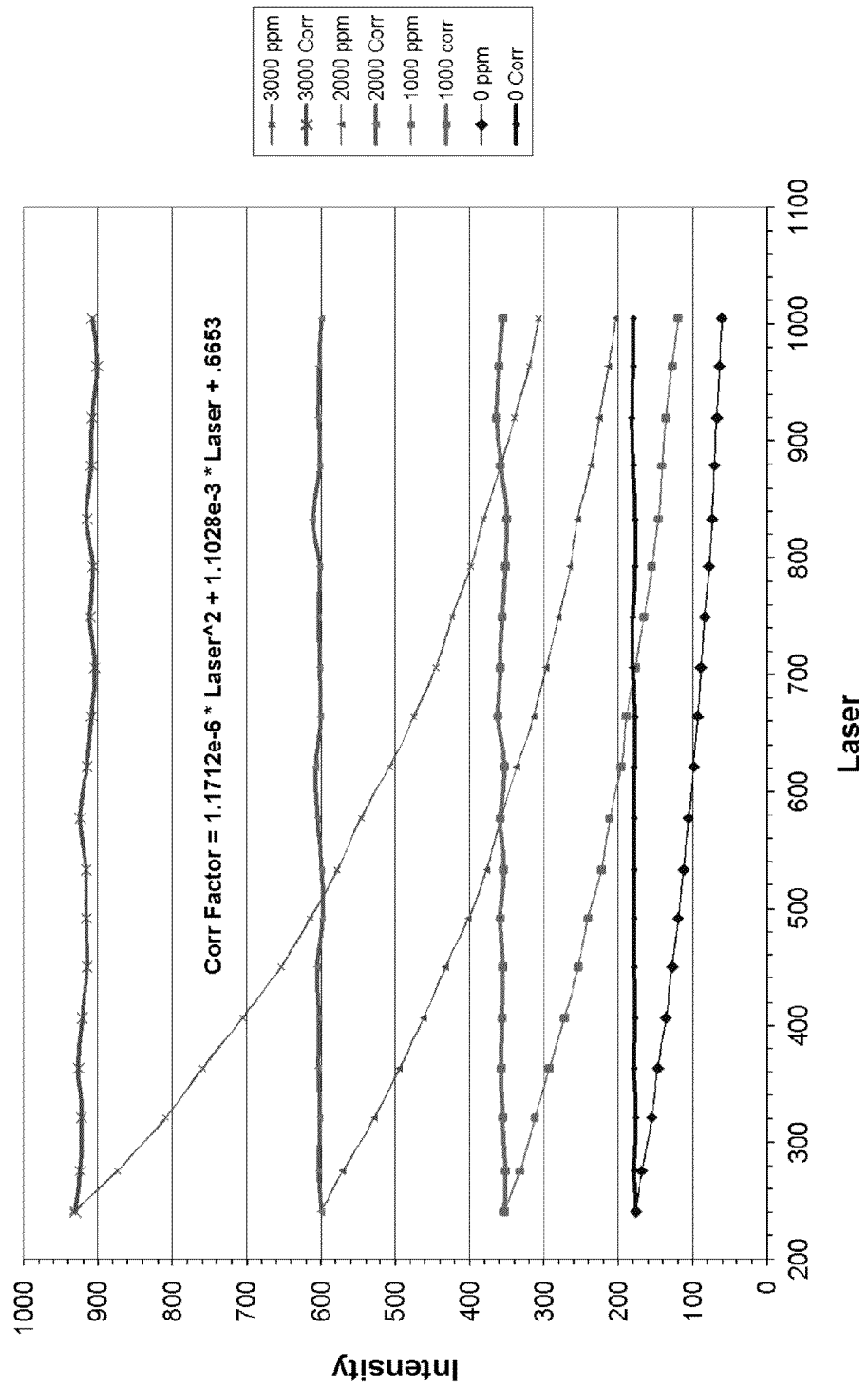
FIG. 12: Fluorescence Intensity: Uncorrected and Corrected for Distance Variation

FLUOROMETRIC METHOD FOR MONITORING SURFACE ADDITIVES IN A PAPERMAKING PROCESS

CROSS REFERENCE TO RELATED APPLICATION

This application is a continuation-in-part of U.S. patent application Ser. No. 12/047,736 filed Mar. 13, 2008, now abandoned itself a continuation-in-part of U.S. patent application Ser. No. 11/942,065 filed Nov. 19, 2007, now abandoned each of which is herein incorporated by reference.

FIELD OF THE INVENTION

This invention pertains to monitoring and optionally controlling the addition of one or more surface additives to a papermaking process.

BACKGROUND OF THE INVENTION

Current practice for measuring the amount of surface additive(s) usually consists of a manual technique of sheet disintegration and/or mass balance calculations that are relative in nature.

In the case of starch pickup at the size press, a papermaker (e.g., a boardmaker) will in many cases grossly over apply the amount of starch added to a papermaking process, in order to ensure enough starch is held on the surface of the sheet for the functional intent. Past trials included metering size press applications, which allowed the reduction of starch via a blade application technique. While this allowed a significant reduction of starch in the range of 50-70%, the risk associated with failures due to unpredicted and uncontrolled variations of starch pickup was too great to overcome. As a result, many papermakers reverted to puddle style size presses in order to ensure enough starch was added to the sheet.

Fluorescence has been employed to measure starch concentrations in the papermaking process, but fluorescence alone can lead to inaccurate or imprecise measurements. A more accurate, precise, and timely measurement of the amount of surface additives on a sheet is therefore desired. This potentially will allow the papermaker to drive addition rates to very low levels, while being able to quickly predict and control statistically out of specification addition rates. Even more desirable is a method that provides for the more accurate and timely measurement of surface additives on a sheet that takes into account flutter amplitude and/or sheet temperature. And even more desirable, the method would additionally measure the ratio of tracer to starch in the surface additive.

SUMMARY OF THE INVENTION

The present disclosure provides for a method of monitoring and optionally controlling the addition of one or more surface additives to a papermaking process comprising the following steps: (a) adding a known amount of one or more surface additives to a papermaking process either alone or in known proportion with a known amount of one or more inert fluorescent tracers, wherein the surface additives can only be added alone when the surface additives are capable of fluorescing; (b) measuring the fluorescence of the surface additives and/or one or more inert fluorescent tracers at a point subsequent to adding the surface additives and after a sheet has been formed, wherein the surface additives can only be measured when they are capable of fluorescing and wherein fluorescence is measured with a reflectance based fluorometer; (c) correlating the amount of fluorescence of the surface additives when they are capable of fluorescing and/or inert fluorescent tracers on a sheet with the concentration of the surface additives in a coating on a sheet and/or thickness of a coating on a sheet; and (d) optionally controlling the addition of one or more surface additives to a papermaking process by adjusting the amount of the surface additives added to the papermaking process in response to the coating thickness on a sheet and/or concentration of the surface additives in a coating on a sheet.

A method of monitoring and optionally controlling the addition of one or more surface additives to a papermaking process comprising the following steps: a) adding a known amount of a composition containing one or more surface additives to a papermaking process either alone or in known proportion with a known amount of one or more inert fluorescent tracers, wherein the composition containing the surface additives can only be added alone when the surface additives are capable of fluorescing; b) measuring the fluorescence of the surface additives and/or one or more inert fluorescent tracers at a point prior to sheet formation; c) optionally measuring the fluorescence of the composition containing the surface additives and/or one or more inert fluorescent tracers at a point subsequent to adding the surface additives and after a sheet has been formed, wherein the surface additives can only be measured when they are capable of fluorescing and wherein fluorescence is measured with a reflectance based fluorometer; d) correlating the amount of fluorescence of the surface additives when they are capable of fluorescing and/or inert fluorescent tracers with the concentration of the surface additives, and if step c) occurs, then correlating the amount of fluorescence of the surface additives when they are capable of fluorescing and/or inert fluorescent tracers on a sheet with the concentration of the surface additives in a coating on a sheet and/or thickness of a coating on a sheet; and e) optionally controlling the addition of the composition containing one or more surface additives to a papermaking process by adjusting the amount of the surface additives added to the papermaking process in response to the concentration of the surface additives, and if step c) occurs, then optionally controlling the addition of the composition containing one or more surface additives to a papermaking process by adjusting the amount of the surface additives added to the papermaking process in response to the coating thickness on a sheet and/or concentration of the surface additives in a coating on a sheet.

A method of monitoring and optionally controlling the addition of one or more surface additives to a papermaking process comprising the following steps: a) adding a known amount of a composition containing one or more surface additives to a papermaking process either alone or in known proportion with a known amount of one or more inert fluorescent tracers, wherein the composition containing the surface additives can only be added alone when the surface additives are capable of fluorescing; b) measuring the fluorescence of the surface additives and/or one or more inert fluorescent tracers in an apparatus that serves to hold or feed or apply an aqueous composition into said papermaking process; c) optionally measuring the fluorescence of the composition containing the surface additives and/or one or more inert fluorescent tracers at a point subsequent to adding the surface additives and after a sheet has been formed, wherein the surface additives can only be measured when they are capable of fluorescing and wherein fluorescence is measured with a reflectance based fluorometer; d) correlating the amount of fluorescence of the surface additives when they are capable of fluorescing and/or inert fluorescent tracers with the concentration of the surface additives, and if step c) occurs, then correlating the amount of fluorescence of the surface additives when they are capable of fluorescing and/or inert fluorescent tracers on a sheet with the concentration of the surface additives in a coating on a sheet and/or thickness of a coating on a sheet; and e) optionally controlling the addition of a composition containing one or more surface additives to a papermaking process by adjusting the amount of the surface additives added to the papermaking process in response to the concentration of the surface additives; and if step c) occurs, then optionally controlling the addition of a composition containing one or more surface additives to a papermaking process by adjusting the concentration of the surface additives in the apparatus in response to coating thickness on a sheet and/or concentration of the surface additives in a coating on a sheet.

Another embodiment of the invention is a method of fluorometrically monitoring and optionally controlling the addition of at least one surface additive to a papermaking process. The papermaking process comprises forming a sheet. The sheet has a temperature and a flutter amplitude. The method comprises the steps of first measuring the fluorescence of a composition prior to the composition being added to the papermaking process; adding a known amount of the composition to the papermaking process after the forming of the sheet; second measuring the fluorescence of the sheet; third measuring the temperature of the sheet using the non-contact sensor; optionally fourth measuring the flutter amplitude using the displacement sensor; correcting the second measuring using the measured sheet temperature; first correlating the measured fluorescence of the composition with the concentration of the at least one surface additive in the composition; second correlating the corrected measured fluorescence of the sheet with the concentration of the at least one surface additive in the composition; and optionally controlling at least a portion of the papermaking process and/or the addition of the at least one surface additive based on any of the measurements.

The composition comprises a concentration of the at least one surface additive. The second measuring is performed with a fluorometer apparatus. The fluorometer apparatus comprises a fluorometer, a non-contact temperature sensor, and optionally a displacement sensor. The fluorometer comprises a dichroic mirror and at least two fluorescence detectors. The process may include the additional step of determining a coating thickness of the composition on the sheet based on the second correlating step.

Additionally, if the at least one surface additive is incapable of fluorescing, then the composition further comprises an inert fluorescent tracer. When present, the inert fluorescent tracer in the composition is present in known proportion with a known amount of the at least one surface additive.

Yet another embodiment of the invention is an apparatus for monitoring and optionally controlling the addition of at least one surface additive to a papermaking process. The papermaking process comprising a sheet, and the sheet has a temperature and a flutter amplitude. The apparatus comprises a fluorometer, a temperature sensor, and a displacement sensor. The fluorometer comprises an ultraviolet light source, a fluorescence detector, a reference detector, a reference reflector, a dichroic mirror, and optionally an electronic control unit. The ultraviolet light source is operably positioned to shine ultraviolet light onto the dichroic mirror and the reference reflector, with a portion of the ultraviolet light reflected by the reference reflector to the reference detector, and another portion of the ultraviolet light reflected by the dichroic mirror onto the sheet. The fluorescence detector measures light fluoresced from the sheet. The fluoresced light passes through the dichroic mirror and into the fluorescence detector. The temperature sensor is a non-contact sensor that is operably positioned to measure the temperature of the sheet. The displacement sensor is operably positioned to measure the flutter amplitude of the sheet.

These and other features and advantages of the present invention will be apparent from the following detailed description, in conjunction with the appended claims.

BRIEF DESCRIPTION OF THE DRAWINGS

The benefits and advantages of the present invention will become more readily apparent to those of ordinary skill in the relevant art after reviewing the following detailed description and accompanying drawings, wherein:

FIG. 12 is a graph of sheet fluorescence, several plot lines uncorrected for sheet flutter amplitude and several other plot lines corrected for sheet flutter amplitude.

DETAILED DESCRIPTION OF THE INVENTION

Figure 1:
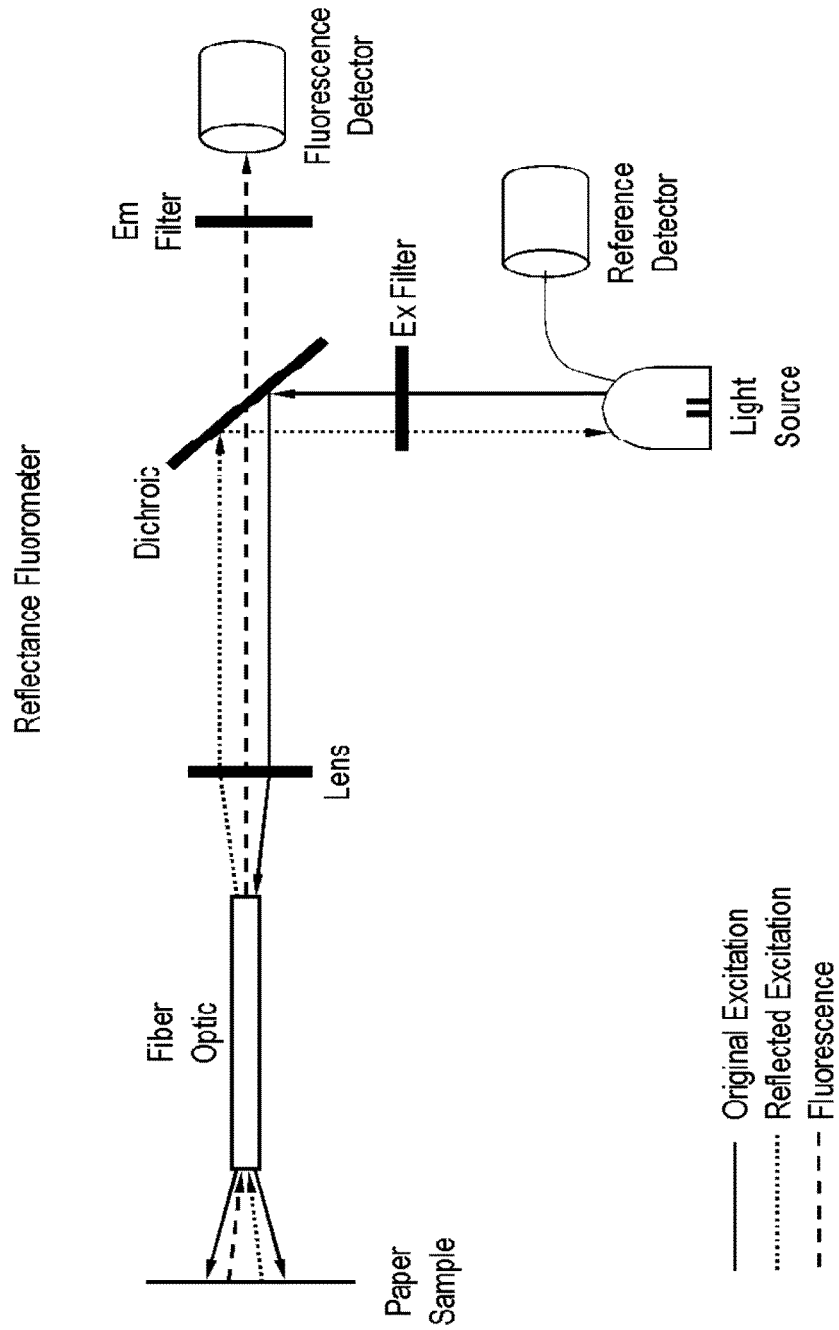
FIG. 1 shows a schematic of how a reflectance-based fluorometer would work in one embodiment of the invention.

Definitions:

"Papermaking process"/"papermaking processes" refer to a method(s) of making any kind of paper products (e.g., paper, tissue, board, etc.) from pulp comprising forming an aqueous cellulosic papermaking furnish, draining the furnish to form a sheet and drying the sheet. The steps of forming the papermaking furnish, draining and drying may be carried out in any conventional manner generally known to those skilled in the art. The papermaking process/processes may also include a pulping stage, i.e. making pulp from woody raw material and bleaching stage, i.e. chemical treatment of the pulp for brightness improvement. Moreover, the papermaking process includes all processing steps applied to a paper sheet up till the end-user receives and optionally analyzes the paper sheet prior to use of the paper product.

"Sheet"/"sheets" refer to sheet(s) formed as a result of or during a papermaking process/papermaking processes. The term "paper sheet"/"paper sheets" are used interchangeably with the term "sheet"/"sheets."

"Surface additive"/"surface additives" refer to papermaking additive(s) that impart one or more chemical and/or physical (e.g., mechanical) properties on a sheet surface. For example, the sheet can be a paper sheet, tissue sheet, board sheet, or any other type of sheet produced by a papermaking process. For example, an imparted chemical property may allow "ink" to bind to the paper in a more efficacious manner.

"Element A and/or Element B" means that either Element A, or Element B, or both Element A and Element B is present for a given situation.

While the present invention is susceptible of embodiment in various forms, there is shown in the drawings and will hereinafter be described several presently preferred embodiments with the understanding that the present disclosure is to be considered an exemplification of the invention and is not intended to limit the invention to the specific embodiment illustrated.

It should be further understood that the title of this section of this specification, namely, "Detailed Description of the Invention," relates to a requirement of the United States Patent Office, and does not imply, nor should be inferred to limit the subject matter disclosed herein.

As mentioned above, one way of measuring the starch concentration employs fluorescent tracing. The method involves measuring the fluorescence of the surface additive compound before it is added to the sheet, and then measuring the fluorescence of the sheet. Several variables can affect the accuracy and/or precision of the measurements. Included in these variables are sheet flutter amplitude, sheet temperature, and tracer-to-starch ratio in the compound. Sheet flutter can cause errors in the measurement of coating thickness using fluorescent tracing technology. Variations in sheet temperature can also cause variations in fluorescent intensity.

A critical parameter that should be known by the paper manufacturer is the tracer-to-starch ratio in the surface additive. Because the starch and tracer streams are typically independent of each other and can vary, the ratio can change unknowingly during the papermaking process.

Preferred Embodiments:

As described above, one or more surface additives added to a papermaking process are tracked by a fluorometric-based protocol. This requires that the medium exposed to fluorescence is suitable for fluorometric measurement, e.g., the entire film depth of a coating is excited and its emission collected. One of ordinary skill in the art could determine this without undue experimentation.

The fluorometric protocol includes the following approaches: (1) the one or more surface additives are capable of fluorescing, inherent and/or modified to fluoresce, e.g., with a fluorescent moiety or by reacting with an in-system molecule or by other means aside from inherent characteristics, (2) one or more inert fluorescent tracers are added in known proportion with the surface additives, or (3) a combination thereof.

When a surface additive is capable of fluorescing, the fluorescence can be directly correlated to the concentration of the surface additive in a coating/thickness of a coating containing the surface additive, e.g., by calibrating fluorescence intensity with the concentration of the surface additive and/or thickness of a coating containing the surface additive. One of ordinary skill in the art could carry out this procedure without undue experimentation.

In one embodiment, the surface additives are inherently fluorescent.

In another embodiment, a fluorescent moiety can be covalently attached to the non-fluorescent surface additives. Therefore, the functionalized surface additives have fluorescent properties.

When an inert fluorescent tracer is involved, the inert fluorescent tracer is added in known proportion with the surface additive. The amount of surface additive or thickness of a coating containing a surface additive can be inferred from the fluorescence of the inert fluorescent tracer, e.g., by calibrating fluorescence intensity with concentration of the additive in a coating on a sheet and/or thickness of a coating containing the additive on a sheet. One of ordinary skill in the art could carry out this procedure without undue experimentation.

In one embodiment, the inert fluorescent tracers can be added to a coating formulation at a specific known concentration such that by measuring the concentration of inert fluorescent tracers, the amount of the coating on a sheet or surface additives in a coating on a sheet can be inferred.

It may also be possible to monitor both a surface additive that is fluorescent and an inert fluorescent tracer. The amount of the coating on a sheet or surface additives in a coating on a sheet can be inferred from the fluorescence of the inert fluorescent tracer and fluorescence of the surface additive, by calibrating fluorescence intensity with concentration of the additive in a coating on a sheet and/or thickness of a coating containing the additive on a sheet. One of ordinary skill in the art could carry out this procedure without undue experimentation.

Various types of one or more inert fluorescent tracers may be utilized for this invention.

One of ordinary skill in the art would know what an inert fluorescent tracer is.

In one embodiment, an inert fluorescent tracer is a substance, which is chemically non-reactive with any components in the papermaking process and does not itself degrade with time. It is completely soluble in the system at all relevant levels of concentration. Its fluorescence intensity is always/substantially proportional to its concentration and is not quenched or otherwise diminished by the system.

In another embodiment, an inert fluorescent tracer is an inert fluorescent tracer that is not appreciably or significantly affected by any other chemistry in a papermaking process. To quantify what is meant by "not appreciably or significantly affected", this statement means that an inert fluorescent compound has no more than a 10% change in its fluorescent signal, under conditions normally encountered in papermaking process. Conditions normally encountered in a papermaking process are known to people of ordinary skill in the art of a papermaking process.

In another embodiment, the desired characteristics for an inert fluorescent tracer, preferably include: high water solubility, excellent chemical stability, good fluorescence properties at manageable wavelengths (e.g., not be quenched by other additives in the sheet/paper sheet/board components), and can be monitored in the presence of common optical brightening agents, e.g., outside the wavelength of optical brighteners to prevent interference between optical brighteners and inert fluorescent tracers.

In another embodiment, the inert fluorescent tracer is a FDA-approved tracer, which is required, for example, in food packaging.

In one embodiment, one or more inert fluorescent tracers are selected from the group consisting of at least one of the following: fluorescein or fluorescein derivatives, rhodamine or rhodamine derivatives, a sulfonate salt of naphthalene, a sulfonate salt of pyrene, a sulfonate salt of stilbene, a sulfonate salt of biphenyl, phenylalanine, tryptophan, tyrosine, vitamin A (retinol), vitamin B2 (riboflavin), vitamin B6 (pyridoxin), vitamin E (α-tocopherols), NADH, ATP, ethoxyquin, caffeine, vanillin, naphthalene sulfonate formaldehyde condensate, a phenyl sulfonate formaldehyde condensate, sulfonated lignin, a polymer containing at least one of the following moieties naphthalene sulfonates, pyrene sulfonates, biphenyl sulfonates, or stilbene sulfonates.

Depending on the papermaking process, the optimum concentration of inert fluorescent tracers will vary. One of ordinary skill in the art can determine the amount of inert fluorescent tracers without undue experimentation. Preferably, e.g., in the case of starch, higher concentrations of inert fluorescent tracers work better than lower concentrations of inert fluorescent tracers.

When measuring a paper sheet or solid surface, the fluorometer utilized should be a reflectance-based fluorometer since it is desired to determine the thickness of an applied thin coating onto the surface of an opaque sheet. One or more may be utilized.

A reflectance-based fluorometer is available from Nalco Company or Ocean Optics, Dunedin, Fla.

A diagram of one embodiment of a reflectance-based fluorometer is given in FIG. 1. The reflectance fluorometer uses an optical fiber to excite the tracer on a sheet and monitor its reflected fluorescence. A suitable light source, such as an LED, xenon flash lamp or discharge lamp provides the excitation light. The raw source light is filtered by a suitable excitation filter (available from Semrock, Inc./Andover, Inc.) to remove unwanted wavelengths in the fluorescence emission region. The light is reflected at 90 degrees and additionally filtered by a dichroic filter to give a new beam along a different direction. The beam is focused onto the core of a fiber optic cable by an appropriate lens. The other end of the fiber optic is positioned close to or touching the surface of the paper sheet in order to illuminate a region of its surface causing fluorescence emission. The emission is captured by the same fiber which carries the reflected light back to the lens where it is collimated and directed back onto the dichroic filter. Reflected excitation light is reflected back to the source while the fluorescence passes straight through to an emission filter. A suitable optical detector, such as a photodiode or photomultiplier tube, detects the filtered light. An optional reference detector can be used to correct for varying light source intensity.

Other designs for reflectance-based fluorometers would be apparent to one of ordinary skill in the art.

Other types of fluorometers may be utilized, especially in cases where fluorescence of a non-solid surface is measured.

In one embodiment, a handheld or benchtop fluorometer can be used when measuring the wet-end of a papermaking process prior to sheet formation or when one is measuring fluorescence of an aqueous composition of surface additives in an apparatus wherein the sample is collected and put into a cuvette that is inserted into the fluorometer. Alternatively, a fiber optic based handheld or benchtop fluorometer can be used wherein the probe is immersed in the collected sample for a fluorescence reading.

In another embodiment, an in-line fluorometer can be used when measuring the wet-end of a papermaking process prior to sheet formation or when one is measuring fluorescence of an aqueous composition of surface additives in an apparatus wherein the sample flows through a suitable flow cell in which sample fluorescence can be continuously measured. Alternatively, a fiber optic based, in-line fluorometer can be used wherein the probe is mounted such that it is immersed in the sample or mounted in a flow cell for a fluorescence measurement.

Various types of surface additives may be utilized in the present invention.

In one embodiment, the surface additives are selected from the group consisting of at least one of the following: starch, pigments, binders, plasticizers, and other additives to improve the physical properties of a paper/board sheet, including surface strength, brightness, printability, water resistance, or adhesion of subsequent coatings.

In another embodiment, the surface additives contain a covalently bonded fluorescent moiety.

In another embodiment, the starch contains a covalently bonded fluorescent moiety.

The surface additives may be added at various stages in the papermaking process.

In one embodiment, the surface additives are added between a forming section of a papermaking process and a press section of a papermaking process.

In another embodiment, the surface additives are added at the wet-end of a papermaking process.

In another embodiment, the surface additives are added to a papermaking process between or at a water box and a sheet.

The fluorescence of the sheet may be measured at various points in the papermaking process.

In one embodiment, the fluorescence is measured at some point after the press section.

In another embodiment, the fluorescence is measured after the dryer section of a papermaking process.

In another embodiment, the fluorescence is measured after a dry line in a forming section.

In another embodiment, the fluorescence is measured proximate to the press section.

In another embodiment, the fluorescence is measured in a papermaking process after a paper is converted to a narrow web or a sheet before end use.

In another embodiment, the fluorescence of starch containing a covalently bonded fluorescent moiety and/or fluorescence of inert fluorescent tracers added in known proportion with the starch is measured after a dryer section and before a coating section of a papermaking process.

In another embodiment, the fluorescence of the surface additives and/or fluorescence of inert fluorescent tracers added in known proportion with said surface additives, excluding starch, are measured after the coating section of a papermaking process.

Fluorescence may be measured at a fixed point (one point), e.g., a measurement in the machine-direction, or at plurality of points, e.g., scanning a plurality of points across the sheet in a cross-directional manner relative to the direction of travel of the paper sheet. A reflectance fluorometer may be utilized in various ways to carry out this task. One of ordinary skill in the art would appreciate various ways of carrying out this task.

In one embodiment, the fluorescence is measured at one point or a plurality of points.

In another embodiment, the fluorometer may be configured to measure in the machine direction, e.g., positioned at a fixed point.

In another embodiment, the measurement of a plurality of points occurs by scanning a fluorometer in a cross-directional manner relative to the direction of said sheet in said papermaking process, similar to the way other sheet monitoring instruments such as brightness or basis weight probes do.

In another embodiment, the fluorometer is configured so that on-line measurements can be taken.

A controller may be utilized to implement the above-referenced protocol.

One or more controllers are in communication with the fluorometer and are programmed with an algorithm to collect said fluorescence measurements, correlate the amount of fluorescence of the surface additives when they are capable of fluorescing and/or inert fluorescent tracers on a sheet with the concentration of the surface additives in a coating on a sheet and/or thickness of a coating on a sheet; and optionally adjust the amount of the surface additives added to the papermaking process in response to the coating thickness on a sheet and/or concentration of the surface additives in a coating on a sheet in accord with a pre-determined protocol.

Adjusting the amount of the surface additives added to the papermaking process in response to the coating thickness on a sheet and/or concentration of the surface additives in a coating on a sheet can be done in various ways.

As stated above, a controller can implement this response or it can be done manually through a papermaking process operator.

The adjustment can be done by various means.

In one embodiment, adjustment can be done through the use of a spray boom in which the feed rate of the surface additives to the paper sheet can be adjusted.

In another embodiment, one could adjust additive feed rates independently in a plurality of zones across the sheet based on fluorescence readings by scanning a fluorometer in a cross-directional manner relative to the direction of said sheet in said papermaking process.

In another embodiment, one could adjust papermaking process parameters such as sheet speed through the paper machine, and/or sheet moisture.

In another embodiment, the settings of a metering size press can be adjusted in response to the coating thickness on a sheet and/or concentration of the surface additives in a coating on a sheet to maintain a desired thickness or to maximize production tonnage rate or minimize over usage of additives or energy.

In another embodiment, the surface additives are added onto the sheet by one or more mechanisms: spray system, roller coater, blade coater, cast coater, rod coater, air knife coater, curtain coater, flexo coater, gravure coater, and screen coater.

In another embodiment, the apparatus may also include one or more parts of a paper machine in a papermaking process where the surface additives come in contact with a sheet in the papermaking process.

In another embodiment, one can adjust the concentration of surface additives in the apparatus in response to the fluorescence measurements made of one or more samples from the apparatus by a handheld, benchtop, in-line fluorometer, or a combination thereof.

With respect to measuring an apparatus that serves to hold or feed an aqueous composition into the papermaking process, the apparatus may be of various varieties known to those of ordinary skill in the art. In particular, the apparatus may also include parts of the paper machine where the surface additives come in contact with the sheet.

In one embodiment, the aforementioned apparatus is a chemical feeder or receptacle that holds one or more chemicals.

In a further embodiment, the chemicals are surface additives. With respect to the types of chemicals being feed into the process, they can of various types including, but not limited to the ones discussed above.

In an embodiment, the apparatus uses two types of fluorometers to monitor at least one surface additive: one to measure fluorescence of the sheet and one to measure the fluorescence of the composition that comprises the at least one surface additive. The composition fluorometer may be coupled with a refractometer, a temperature sensor, or both.

In an embodiment, the sheet fluorometer comprises a displacement sensor to measure and correct for sheet flutter. The displacement sensor may take the form of a laser displacement sensor. The sheet fluorometer may use a dichroic beamsplitter to separate excitation light from scattered light from the fluorescent intensity.

In an embodiment, one or both of the fluorometers uses a solid state light source to stimulate fluorescence. The solid state light source may comprise an LED light. A preferred wavelength range for at least the sheet fluorometer measurement is about 280 nm.

Figure 3:
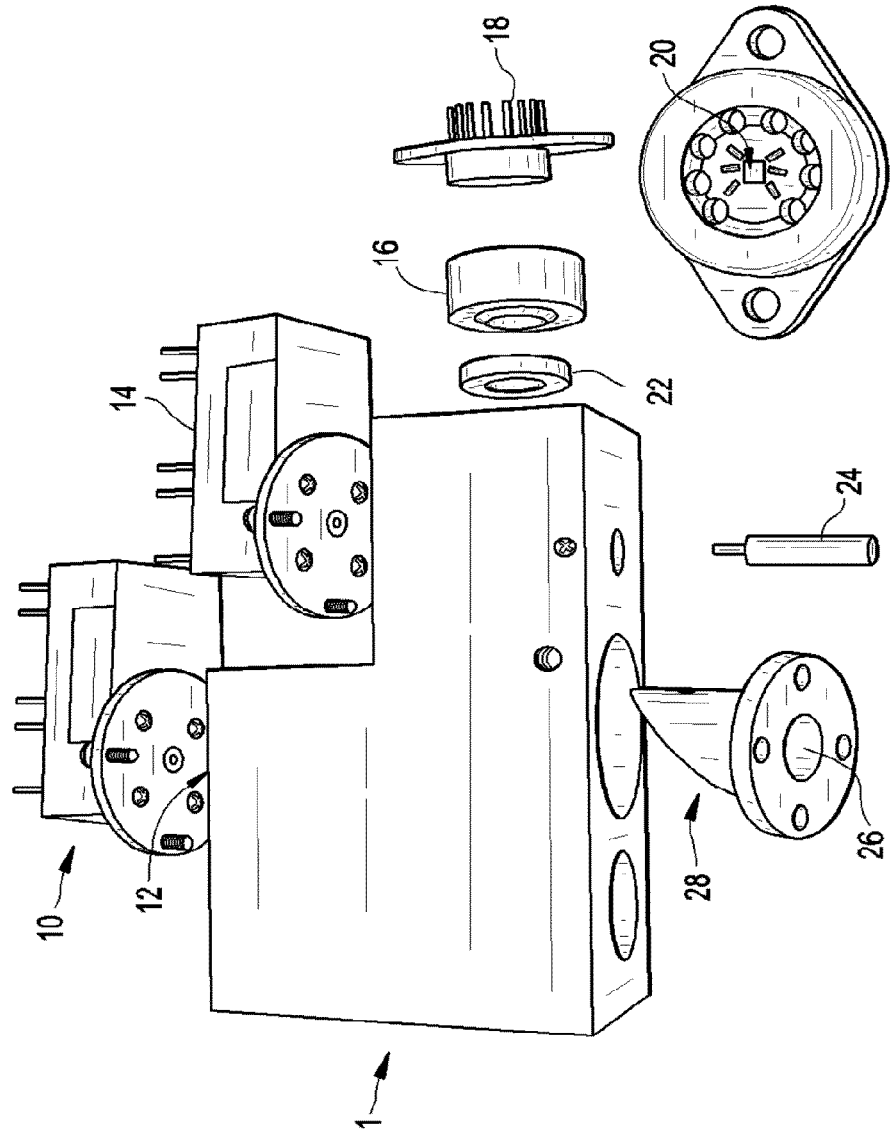
FIG. 3 shows an assembly view of an embodiment of a sheet fluorometer.

Referring to FIG. 3, each figure shows an embodiment of a sheet fluorometer (1) that may be used to practice the invention at hand. The fluorometer comprises a fluorescence detector (10), an emission filter (12), a reference detector (14), an ultraviolet light source (18), a lens (16), an excitation filter (22), a reference reflector (24), and a dichroic mirror (28). The ultraviolet light source (18) may be a windowless LED.

Figure 4:
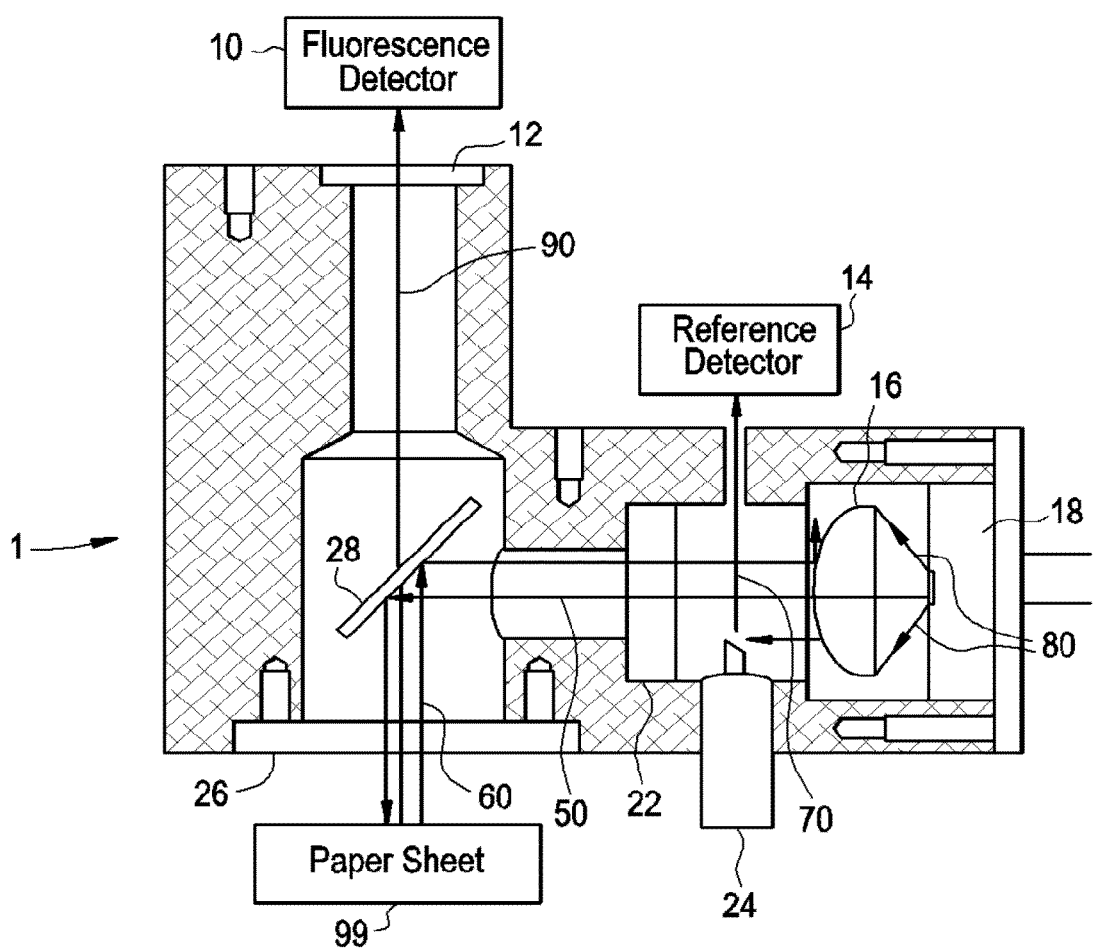
FIG. 4 shows a diagram of the typical operation of an embodiment of a sheet fluorometer.

Referring to FIG. 4, a diagram of a typical cycle of operation of the sheet fluorometer (1) is shown. An ultraviolet light source (18) emits light (80) which passes through a lens (16). The lens (16) focuses the light (80) into a focused beam (50). A portion of the focused beam (50) is reflected by the reference reflector (24) and becomes the reference beam (70). The reference reflector (24) should be relatively small when compared to the size of the focused beam (50), with the reference reflector (24) preferably circular with a diameter of 0.02 to 0.1 inches. The reference beam (70) is passed through an aperture of similar cross-sectional shape and size of the reference reflector (24), and preferably the same cross-sectional shape and size, and into the reference detector (14). Another name for focused beam is excitation beam.

The focused beam (50) passes through the excitation filter (22) and reflects off the dichroic mirror (28), passing through the beam window (26) and onto the paper sheet (99). The light from the paper sheet (99) fluoresces (90) and reflects (60) off the paper sheet (99) and passes back through the beam window (26). The fluorescing beam (90) passes through the dichroic mirror (28) and the emission filter (12), and then into the fluorescence detector (10). The reflecting beam (60) reflects off the paper sheet (99), and again reflects off the dichroic mirror (28), so that the reflecting beam does not enter the fluorescence detector (10).

Figure 5:
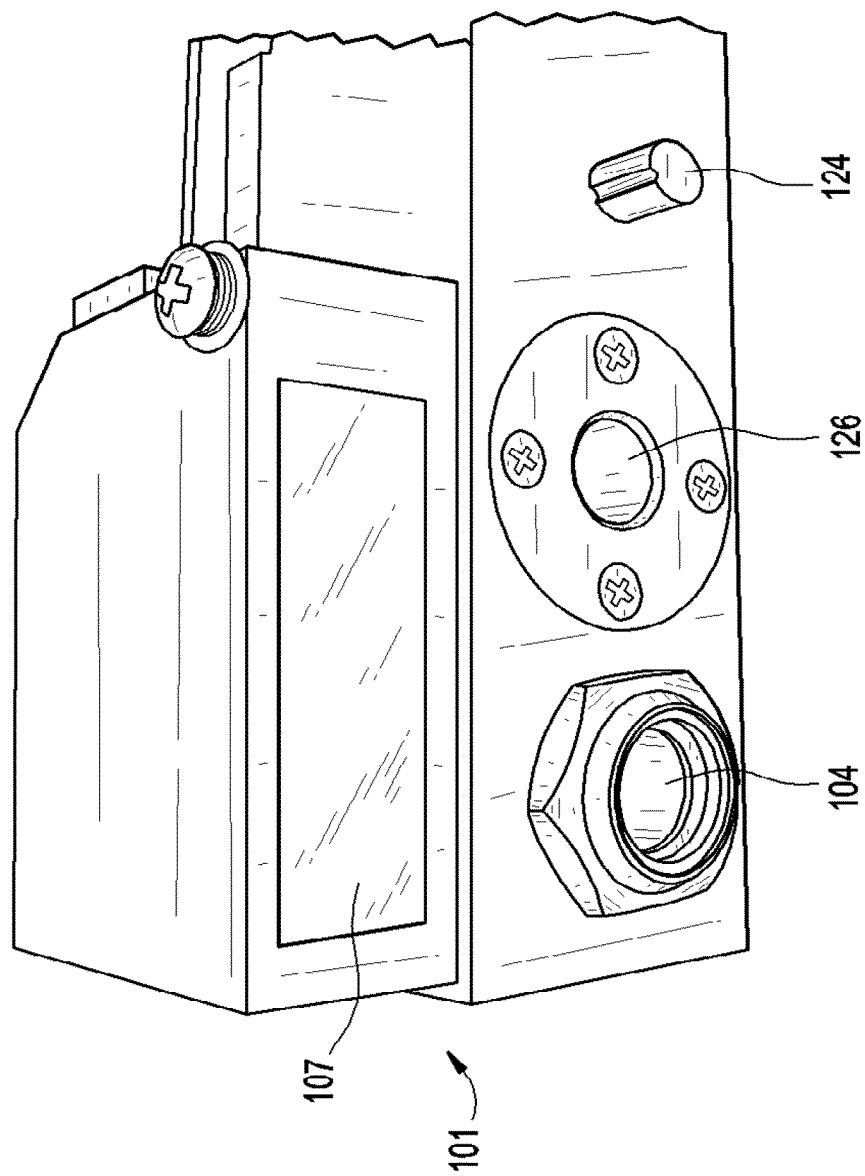
FIG. 5 shows a bottom view of an embodiment of a sheet fluorometer.

FIG. 5 shows a bottom view of an alternate embodiment of the sheet fluorometer (101). In addition to the standard embodiment shown in FIG. 3 and FIG. 4, the alternate embodiment comprises a displacement sensor (107) and a non-contact temperature sensor (104), along with the beam window (126) and the reference reflector (124). The non-contact temperature sensor (104) provides the ability to conveniently measure temperature, which may be valuable to the user. The non-contact temperature sensor (104) may be an infrared temperature sensor. The displacement sensor (107) provides a convenient way of measuring the distance from the fluorometer (1) to the paper sheet (99).

Figure 6:
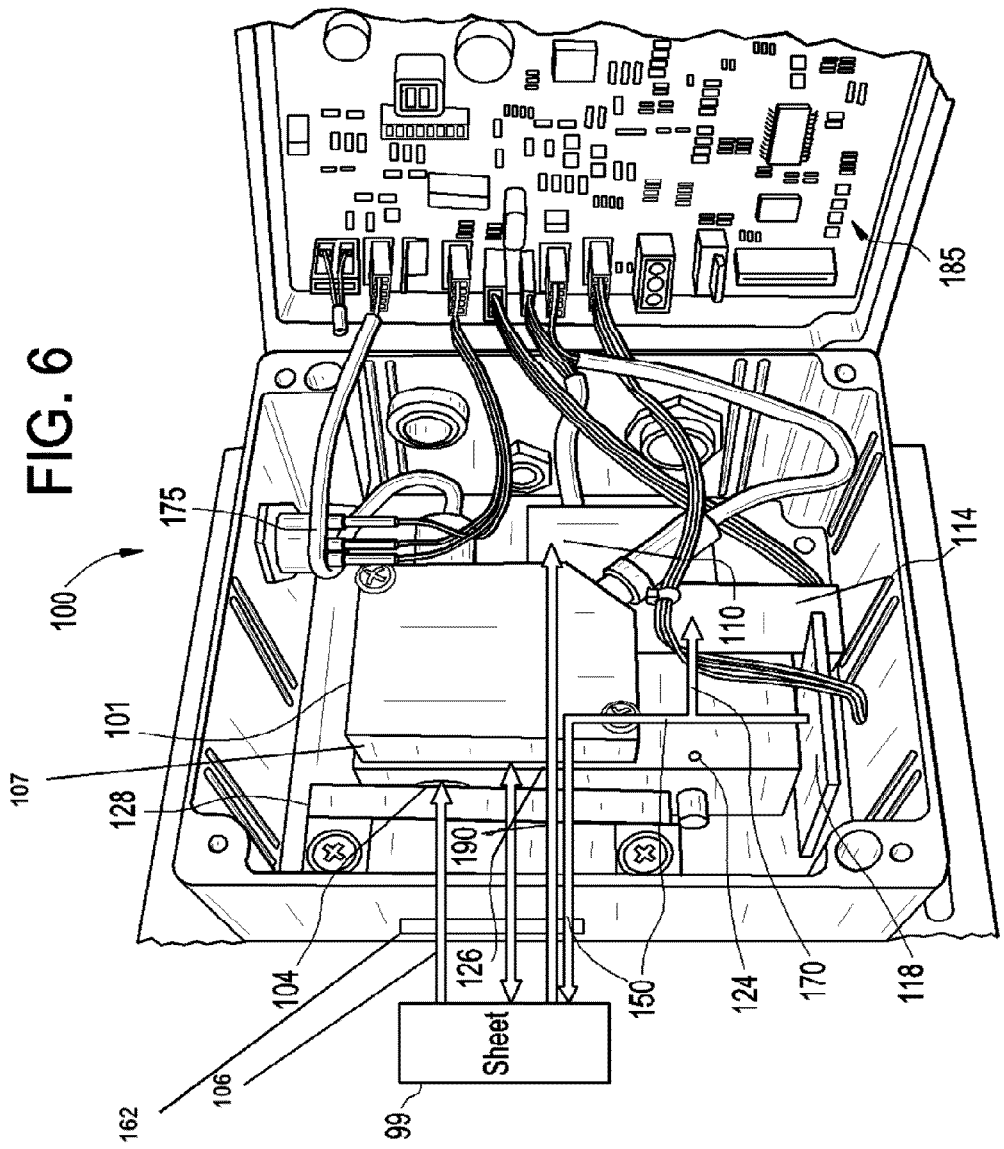
FIG. 6 shows an interior view of an embodiment of a sheet fluorometer apparatus, including a diagram of the typical operation of the embodiment.

Referring to FIG. 6, a diagram of a typical cycle of operation of the sheet fluorometer apparatus (100) is shown, which comprises the sheet fluorometer (101), a non-contact temperature sensor (104), and a displacement sensor (107). An ultraviolet light source (118) emits light (not numbered) which passes through a lens (not shown). The lens focuses the light into a focused beam (150). A portion of the focused beam (150) is reflected by the reference reflector (124) and becomes the reference beam (170). The reference beam (170)

is passed into the reference detector (114). Another name for focused beam is excitation beam.

The focused beam (150) passes through the excitation filter (shown in FIGS. 3 and 4) and reflects off the dichroic mirror (shown in FIGS. 3 and 4), passing through the beam window (126), aperture (162), and onto the paper sheet (99). The light from the paper sheet (99) fluoresces (190) and reflects off the paper sheet (99) and passes back through the aperture (162) and beam window (126). The fluorescing beam (190) passes through the dichroic mirror (shown in FIGS. 3 and 4) and the emission filter (shown in FIGS. 3 and 4), and then into the fluorescence detector (110). When the non-contact temperature sensor (104) takes the form of an infrared temperature sensor, the non-contact temperature sensor (104) measures the infrared light (106) that is emitted from the paper sheet (99). The displacement sensor (107) measures the distance from the displacement sensor (107) to the paper sheet (99). The distance corresponds to the flutter amplitude, which can be measured at any one time or the change over time, all of which are incorporated into the meaning of the term "flutter," "sheet flutter," and "flutter amplitude."

The accessories that make up the apparatus are operatively connected to a control system (185). Additionally, an optional calibration button (175) is shown. One of skill in the art will readily appreciate that the control system (185) can be individually dedicated to a single fluorometer apparatus (100), or may be shared between several fluorometers (101) and any number of several devices described herein or that may make up one or more process operations.

Figure 7:
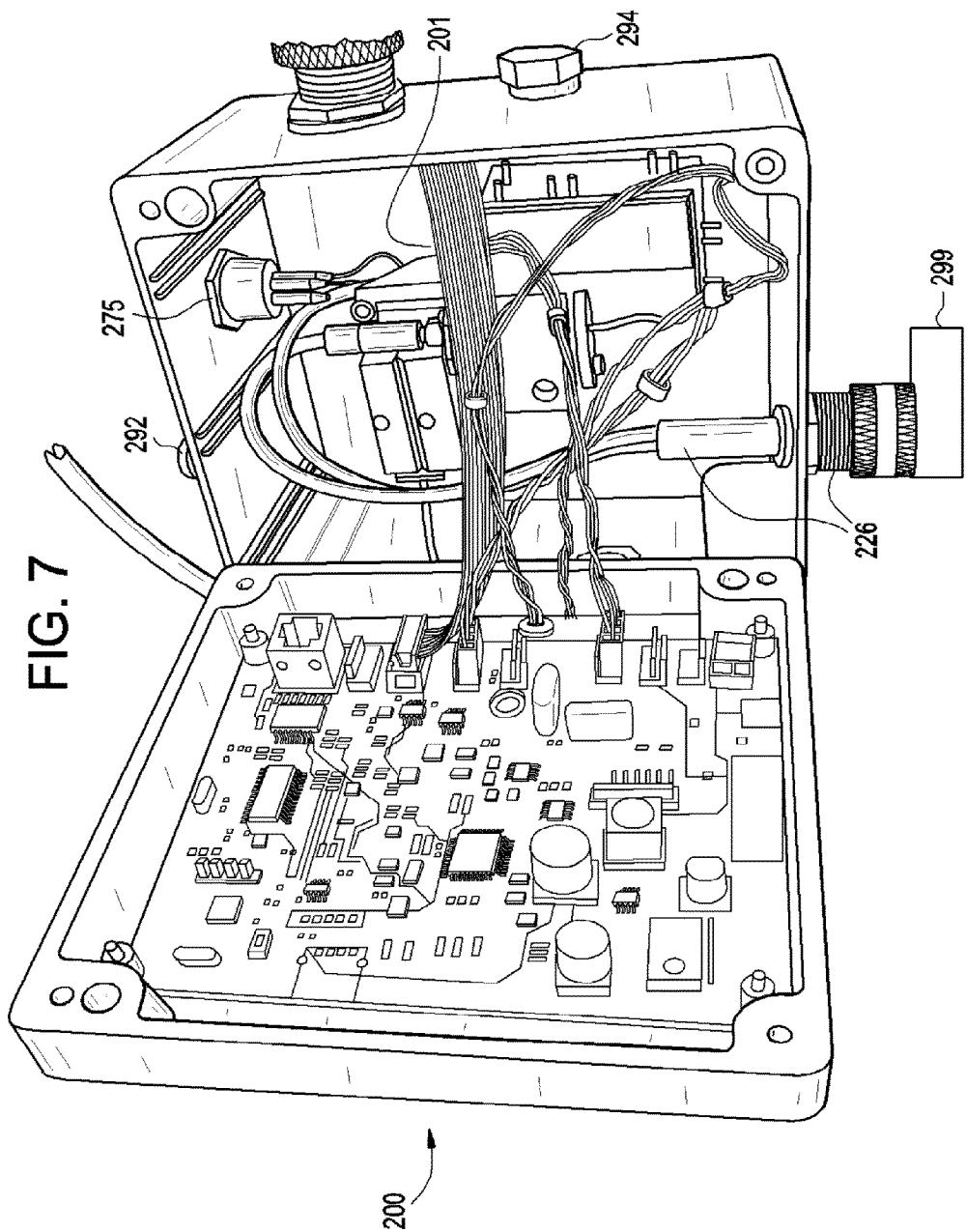
FIG. 7 shows an interior view of an embodiment of a liquid fluorometer apparatus that is equipped with optical fibers.

Referring to FIG. 7, an embodiment of a liquid fluorometer apparatus (200) is shown. The liquid fluorometer apparatus (200) comprises a fluorometer (201) that is constructed and operated in like fashion to the sheet fluorometer shown in FIGS. 3 and 4. The liquid fluorometer apparatus (200) may additionally comprise a fiber optic apparatus (226), a purge in inlet (292), a purge air outlet (294), and a calibration button (275). The tip of the fiber optic apparatus (226) (shown in more detail in FIG. 9) will typically be operatively positioned so that the tip is at least touching the composition (299).

Figure 8:
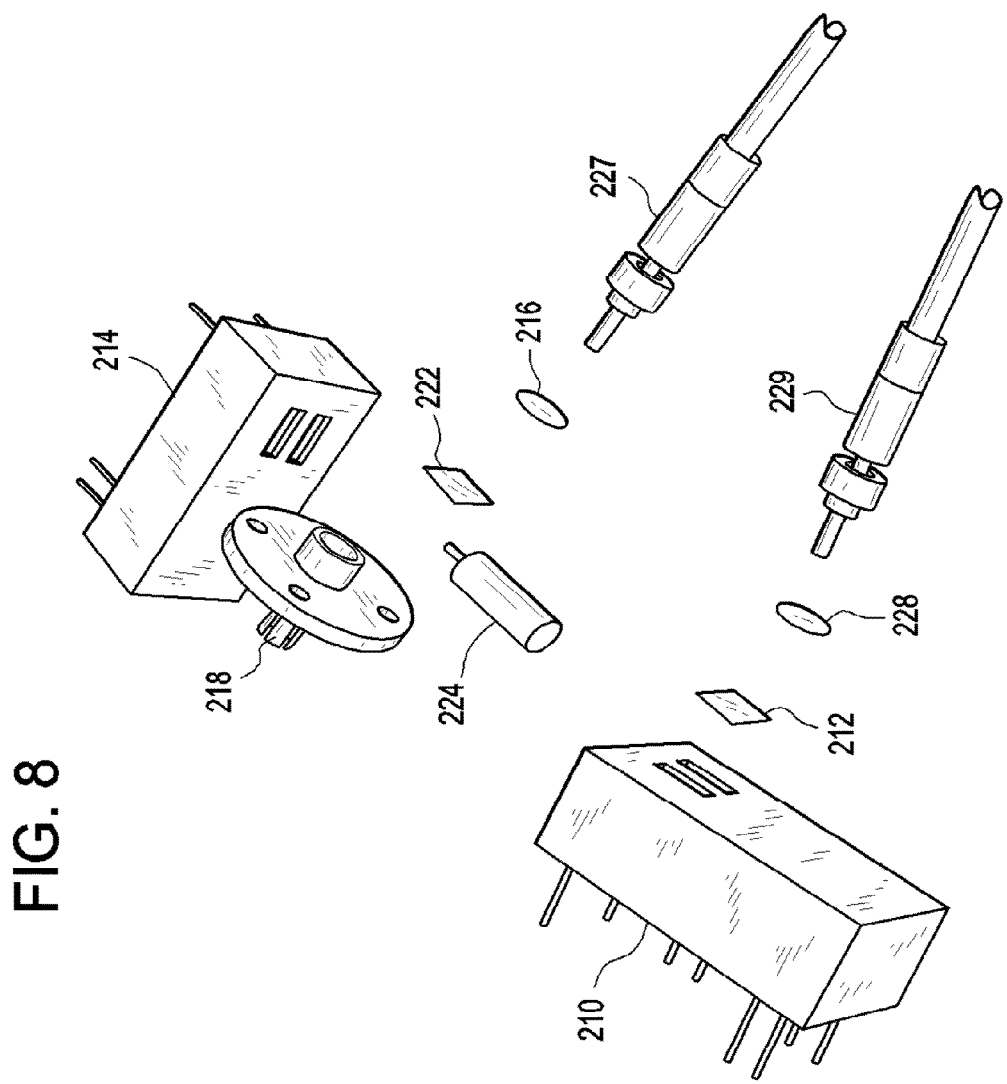
FIG. 8 shows an assembly view of an embodiment of a liquid fluorometer that is equipped with optical fibers.

Referring to FIG. 8, an embodiment of the liquid fluorometer (201) is shown. The liquid fluorometer (201) is constructed and operated in like fashion to the sheet fluorometer shown in FIGS. 3 and 4. The fluorometer comprises a fluorescence detector (210), an emission filter (212), a reference detector (214), an ultraviolet light source (218), a focusing lens (216), an excitation filter (222), and a reference reflector (224). Instead of incorporating a dichroic mirror, the liquid fluorometer (201) may employ the use of a collimating lens (228). The liquid fluorometer (201) additionally employs the use of a fiber optic apparatus (FIG. 7, item 226), with the launch leg (227) and the receiving leg (229) shown. The ultraviolet light source (218) may be a windowless LED.

Figure 9:
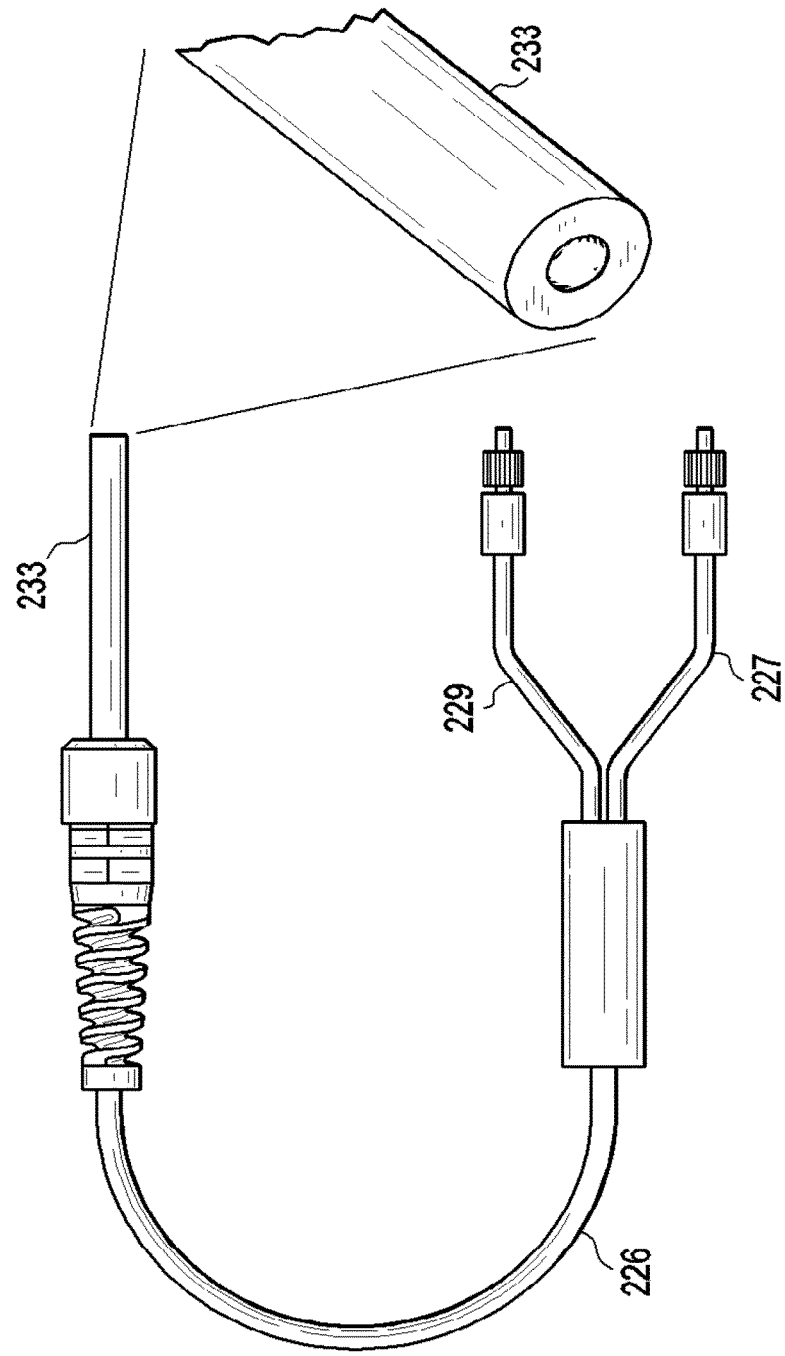
FIG. 9 shows a detailed view of an embodiment of a fiber optic sensor that may be used in conjunction with a liquid fluorometer.

Referring to FIG. 9, a detailed diagram of an embodiment of a fiber optic apparatus 226, which comprises a launch leg (227), a receiving leg (229), and a tip (233). The tip (233) is typically operatively positioned so that the tip (233) is at least touching the composition (FIG. 7, item 299).

Figure 10:
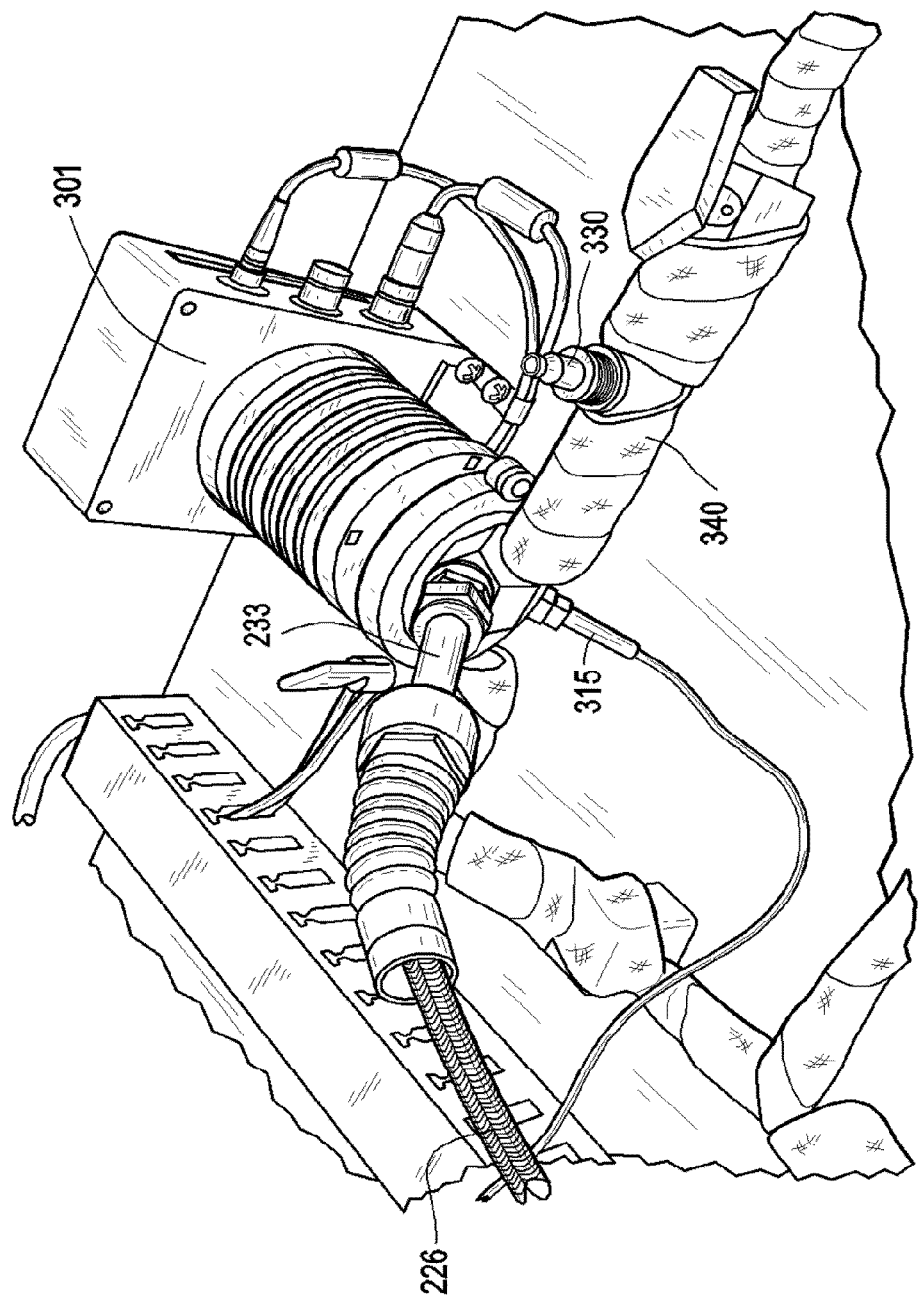
FIG. 10 shows an embodiment of one mounting position of a fiber optic sensor.

Referring to FIG. 10, an embodiment of a fiber optic apparatus (226) mounted onto a refractometer (301) is shown. The composition flows through the sample line (340) into the refractometer (301), passing the tip (233) of a fiber optic apparatus (226) and an optional temperature sensor (315). The optional temperature sensor (315) may be an RTD. The embodiment of FIG. 10 also shows a calibration solution injection port (330).

Figure 11:
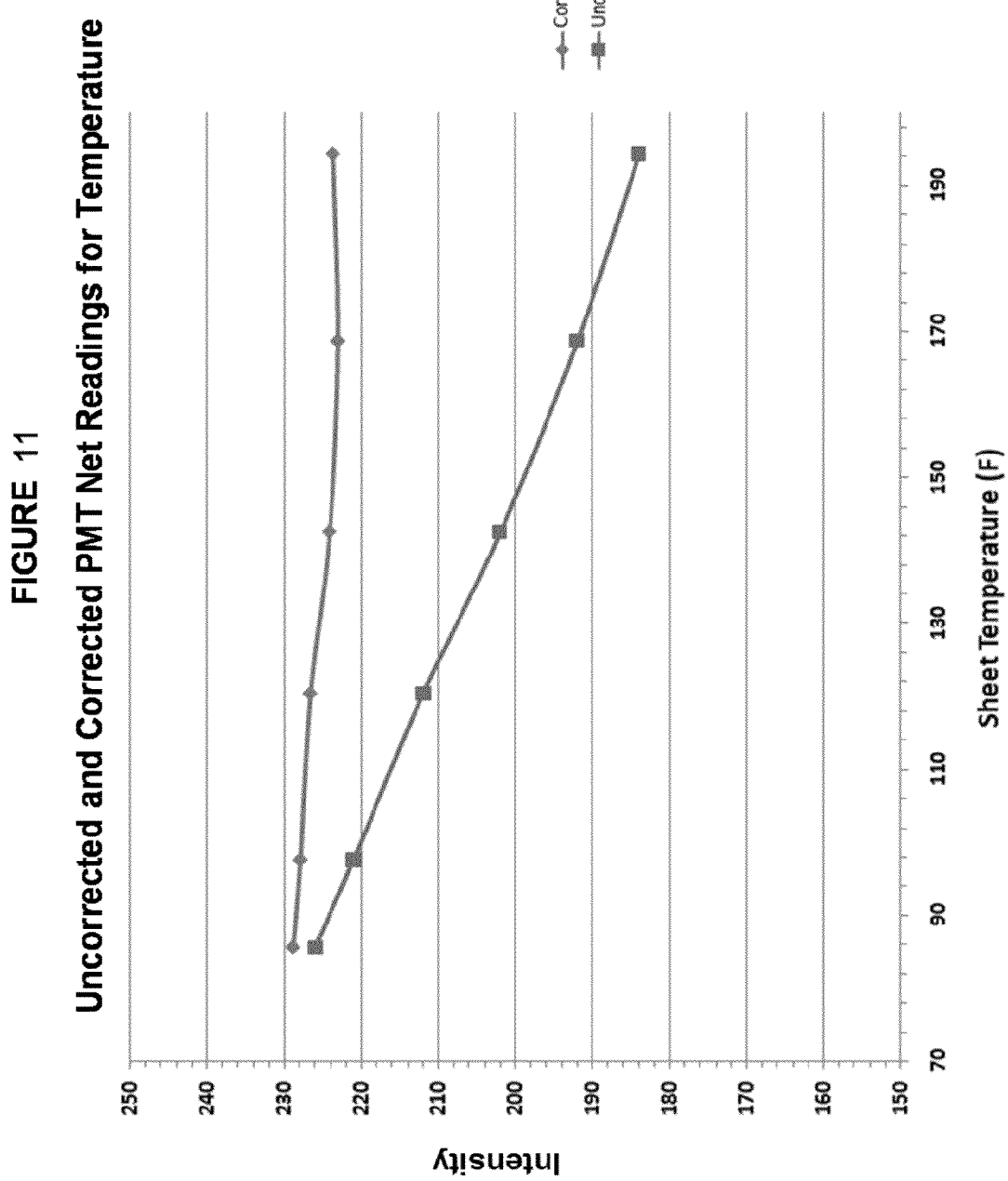
FIG. 11 is a graph of sheet fluorescence, one plot line uncorrected for sheet temperature variation and the other plot line corrected for sheet temperature variation.

FIGS. 11 and 12 show graphical illustrations of fluorescence intensity measurements that are raw and corrected for sheet temperature (FIG. 11) and sheet flutter amplitude (FIG. 12).

In an embodiment, a gas stream is provided in the aperture (162). Such a stream helps to prevent debris and condensation from building in the aperture. The gas can be forced through a vortex cooler to help maintain a constant fluorometer internal temperature. The gas can be air.

In an embodiment, a technique employing pulse mode electronics with peak detection integration is used to keep the LED cool. Additionally, the technique may allow for higher intensity and increase detection signal to noise, allowing for better rejection of ambient light as compared to other techniques.

In an embodiment, a non-contact temperature sensor is incorporated into the measurement device. The non-contact temperature sensor may be an infrared temperature sensor. The non-contact temperature sensor (104) is operably connected to the fluorometer apparatus (100) so that the non-contact temperature sensor (104) measures the sheet temperature. The measured sheet temperature can be used to correct for sheet temperature effects on fluorescent intensity.

In an embodiment, the method of measuring at least one surface additive in the papermaking process measures the fluorescent tracer concentration in the composition as the composition is delivered to the size press. The measurement of fluorescent tracer concentration in the composition stream may be performed using a fiber optic fluorometer. The composition comprises the at least one surface additive and, if necessary, a fluorescent tracer. The at least one surface additive may be a starch compound. The fluorescent tracer is necessary if the at least one surface additive does not fluoresce.

In an embodiment, the surface additive may be comprised of at least one starch. The starch solids concentration may be measured via refractometry. The fluorescent tracer may be measured using a fluorometer, preferably incorporating the use of a fiber optic apparatus. Starch temperature may be measured as well. The measurement of the starch refractometry and temperature allows for an accurate calculation of the ratio of tracer to starch in the starch stream. The ratio of tracer to starch in the starch stream along with the measured sheet fluorescence allows for the accurate calculation of the amount of starch applied in the papermaking process.

In an embodiment, the measured tracer concentration in the starch stream provides an input for the control of the tracer feed pump in a feedback control system. In a preferred embodiment, the feedback control maintains the ratio of tracer to starch at a desired concentration range regardless of any system upsets that may occur.

A fluorometer apparatus or any of the components of a fluorometer apparatus (e.g., fluorometer, temperature sensor, displacement sensor, etc.) may provide input into the papermaking process. The input may provide information that allows the papermaking process and/or the addition of the at least one additive to be controlled. In such a situation, the input would be correlated with at least one value that is measured by a fluorometer apparatus or any of the components of a fluorometer apparatus. The terms "sheet fluorometer," "sheet fluorometer apparatus," "liquid fluorometer," and "liquid fluorometer apparatus" are used solely to differentiate each piece of equipment from the other.

The following examples are not limiting.

EXAMPLES

Protocol

Coat weight or coat thickness testing was performed following a standard testing protocol. Several coating solutions containing various amounts of coating solids were applied to the surface of test sample sheets. Preferably, the solid content and inert fluorescent tracer ratio was kept constant for all solutions. The coat weight on each sample sheet can be varied at the coating application time using various coating techniques. After drying, the dry coat weight, or pick-up, was measured by weight difference. Every individual sample sheet was weighed before and after coating application and the dry coat weight calculated by weight difference. The fluorescence intensity of the dry starch film was measured at several locations for a given sample sheet. The series of fluorescence intensities were then averaged to yield a single fluorescence intensity value for each sample sheet. Two different fluorometers were used to measure the fluorescence intensity of each sample sheet.

Example 1

A test was run following the above-described protocol with three starch solutions containing increasing starch solids while maintaining the starch and inert fluorescent tracer ratio constant. The substrate for each test was an uncoated 21-point paperboard sheet. Each solution was applied on separate sample sheets at four different thicknesses via a manual application method. A fourth starch solution containing no inert fluorescent tracer was also applied to a series of sample sheets for comparison with the traced solutions. The blank used in this trial was an uncoated sample sheet.

Figure 2:
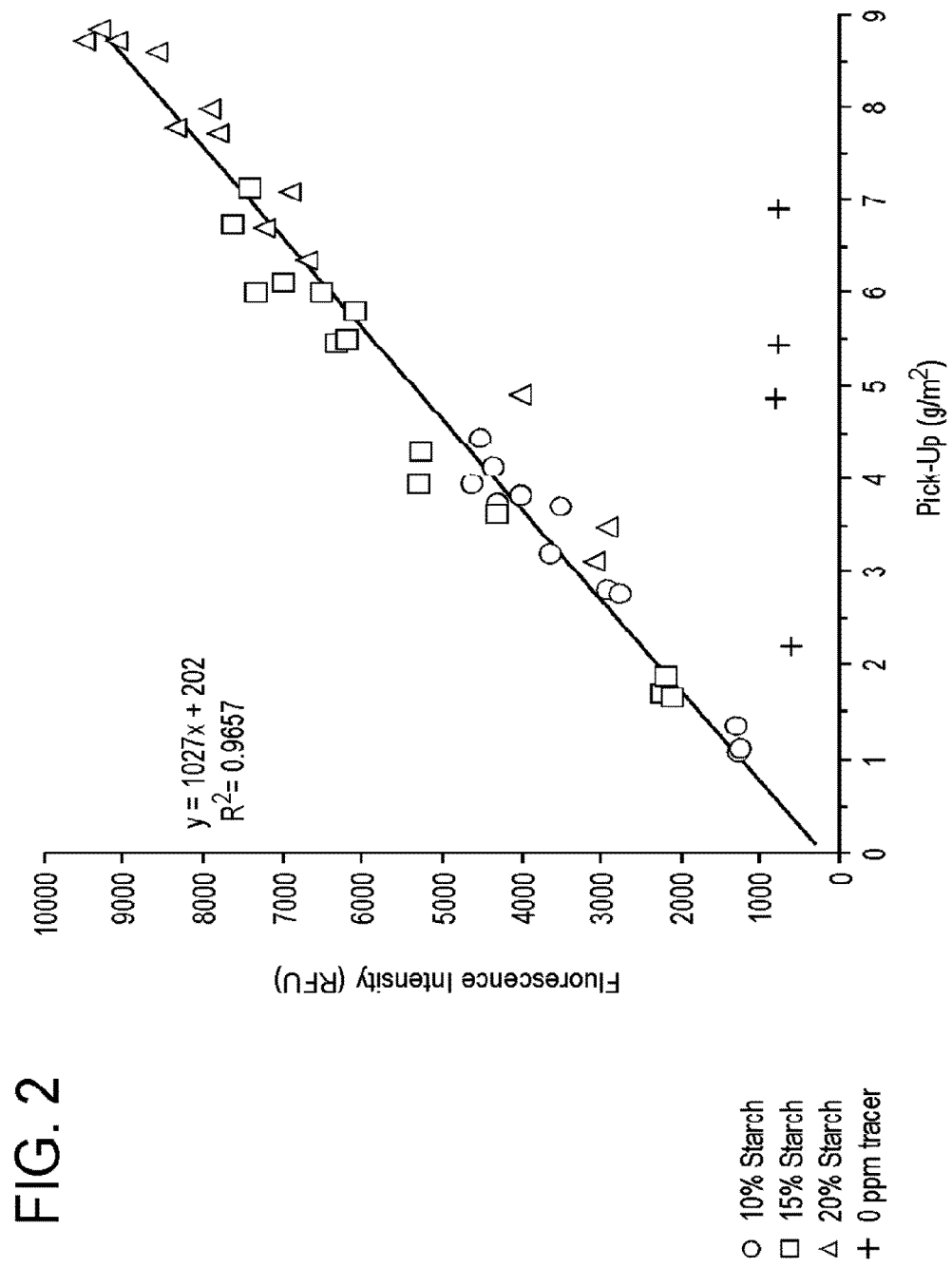
FIG. 2 shows a graph of individual fluorescence vs. individual starch dry pick-up shown by a starch and inert fluorescent tracer combination.

FIG. 2 shows the starch dry coat weight (pick-up, in g/m$^2$) plotted against the fluorescence intensity (in arbitrary units—relative fluorescence units ("RFU")). Each point corresponds to an individual sample sheet. FIG. 2 shows that the measured fluorescence intensities of the entire series of sample sheets measured fall on a line along the plot area diagonal. The linear regression on all points shows very clearly the direct and reliable correlation between the starch dry pick-up and the amount of inert fluorescent tracer present in the layer as measured by fluorescence intensity. The trend line has a y-intercept very close to zero and an $R^2$-factor greater than 0.96. In a few cases, one point is significantly removed from the line. The same stray points were observed with two separate fluorometers, indicating that it is a property of the sample sheet, not an instrument related error. Such points are likely due to defects in the starch layer on the paper web. This data demonstrates that coating defects can be detected with the methods of the claimed invention.

All patents referred to herein, are hereby incorporated herein by reference, whether or not specifically done so within the text of this disclosure.

In the present disclosure, the words "a" or "an" are to be taken to include both the singular and the plural. Conversely, any reference to plural items shall, where appropriate, include the singular. Additionally, the terms "first," "second," "third," etc. are used only to differentiate between steps and not necessarily to indicate the order of a series of steps, unless such order is necessary to perform the method.

From the foregoing it will be observed that numerous modifications and variations can be effectuated without departing from the true spirit and scope of the novel concepts of the present invention. It is to be understood that no limitation with respect to the illustrated specific embodiments or examples is intended or should be inferred. The disclosure is intended to cover by the appended claims all such modifications as fall within the scope of the claims.

We claim:

1. A method of fluorometrically monitoring and optionally controlling the addition of at least one surface additive to a papermaking process, the papermaking process comprising forming a sheet, the sheet having a temperature and a flutter amplitude, the method comprising the following steps:

first measuring the fluorescence of a composition prior to the composition being added to the papermaking process, the composition comprising a concentration of the at least one surface additive;

adding a known amount of the composition to the papermaking process after the forming of the sheet;

second measuring the fluorescence of the sheet, the second measuring performed with a fluorometer apparatus, the fluorometer apparatus comprising a fluorometer, a non-contact temperature sensor, and optionally a displacement sensor, the fluorometer comprising a dichroic mirror and at least two fluorescence detectors;

third measuring the temperature of the sheet using the non-contact temperature sensor;

optionally fourth measuring the flutter amplitude using the displacement sensor;

correcting the second measuring using the measured sheet temperature;

first correlating the measured fluorescence of the composition with the concentration of the at least one surface additive in the composition;

second correlating the corrected measured fluorescence of the sheet with the concentration of the at least one surface additive in the composition;

optionally controlling at least a portion of the papermaking process and/or the addition of the at least one surface additive based on any of the measurements; wherein if the at least one surface additive is incapable of fluorescing, then the composition further comprises an inert fluorescent tracer, the inert fluorescent tracer present in the composition in known proportion with a known amount of the at least one surface additive.

2. A method of fluorometrically monitoring and optionally controlling the addition of at least one surface additive to a papermaking process, the papermaking process comprising forming a sheet, the sheet having a temperature and a flutter amplitude, the method comprising the following steps:

first measuring the fluorescence of a composition prior to the composition being added to the papermaking process, the composition comprising a concentration of the at least one surface additive, the fluorescence corresponding with the concentration of the at least one surface additive in the composition;

adding a known amount of the composition to the papermaking process after the forming of the sheet;

second measuring the fluorescence of the sheet, the second measuring performed with a fluorometer apparatus, the fluorometer apparatus comprising a fluorometer, a non-contact temperature sensor, and a displacement sensor, the fluorometer comprising a dichroic mirror and at least two fluorescence detectors;

third measuring the temperature of the sheet using the non-contact temperature sensor;

fourth measuring the flutter amplitude using the displacement sensor;

correcting the second measuring for variations in the third measuring and/or the fourth measuring;

first correlating the measured fluorescence of the composition with the concentration of the at least one surface additive in the composition;

second correlating the corrected measured fluorescence of the sheet with the concentration of the at least one surface additive in the composition;

determining a coating thickness of the composition on the sheet using the values obtained from the first correlating and the second correlating; and optionally controlling at least a portion of the papermaking process and/or the addition of the at least one surface additive based on any of the measurements; wherein if the at least one surface additive is incapable of fluorescing, then the composition further comprises an inert fluorescent tracer, the inert fluorescent tracer present in the composition in known proportion with a known amount of the at least one surface additive.

3. An apparatus for monitoring and optionally controlling the addition of at least one surface additive to a papermaking process, the papermaking process comprising a sheet, the sheet having a temperature and a flutter amplitude, the apparatus comprising:
   a fluorometer;
   a temperature sensor; and
   a displacement sensor; wherein
   the fluorometer comprising an ultraviolet light source, a fluorescence detector, a reference detector, a reference reflector, a dichroic mirror, and optionally an electronic control unit, wherein the ultraviolet light source is operably positioned to shine ultraviolet light onto the dichroic mirror and the reference reflector,
   a portion of the ultraviolet light reflected by the reference reflector to the reference detector, and another portion reflected by the dichroic mirror onto the sheet,
   the fluorescence detector measuring light fluoresced from the sheet, the fluoresced light passing through the dichroic mirror and into the fluorescence detector;
   the temperature sensor is a non-contact temperature sensor and is operatively positioned to measure the temperature of the sheet; and
   the displacement sensor operatively positioned to measures the flutter amplitude of the sheet.

4. The apparatus of claim 3, wherein the temperature sensor is an infrared temperature sensor.

5. The apparatus of claim 3, wherein the apparatus provides input into the papermaking process, the input controlling at least a portion of the papermaking process, the input correlated with at least one of the following values: detected fluorescence, measured temperature of the sheet, and measured flutter amplitude of the sheet.

6. The apparatus of claim 3, wherein the apparatus includes a second fluorometer, the second fluorometer comprising a fiber optic apparatus.

7. The method of claim 1, wherein the composition is added onto the sheet by at least one of the following mechanisms: spray system, roller coater, blade coater, cast coater, rod coater, air knife coater, curtain coater, flexo coater, gravure coater, and screen coater.

8. The method of claim 2, wherein the composition is added onto the sheet by at least one of the following mechanisms: spray system, roller coater, blade coater, cast coater, rod coater, air knife coater, curtain coater, flexo coater, gravure coater, and screen coater.

9. The method of claim 1, wherein the method further comprises the step of determining a coating thickness of the composition on the sheet based on the second correlating.

10. The method of claim 1, wherein the method further comprises the steps of fifth measuring the temperature of the composition.

11. The method of claim 2, wherein the method further comprises the steps of fifth measuring the temperature of the composition.

12. The method of claim 1, wherein the first measuring is performed using a fluorometer comprising a fiber optic apparatus.

13. The method of claim 2, wherein the first measuring is performed using a fluorometer comprising a fiber optic apparatus.

14. The method of claim 12, wherein the first measuring is performed additionally using a refractometer.

15. The method of claim 13, wherein the first measuring is performed additionally using a refractometer.

* * * * *